United States Patent
Woods

(10) Patent No.: US 8,932,210 B2
(45) Date of Patent: Jan. 13, 2015

(54) MINIMALLY INVASIVE RETRACTION DEVICE HAVING DETACHABLE BLADES

(75) Inventor: Richard W. Woods, Catonsville, MD (US)

(73) Assignee: K2M, Inc., Leesburg, VA (US)

(*) Notice: Subject to any disclaimer, the term of this patent is extended or adjusted under 35 U.S.C. 154(b) by 704 days.

(21) Appl. No.: 12/396,230

(22) Filed: Mar. 2, 2009

(65) Prior Publication Data

US 2009/0221877 A1 Sep. 3, 2009

Related U.S. Application Data

(60) Provisional application No. 61/032,230, filed on Feb. 28, 2008.

(51) Int. Cl.
*A61B 1/32* (2006.01)
*A61B 17/70* (2006.01)

(52) U.S. Cl.
CPC .......... *A61B 17/7085* (2013.01); *A61B 17/7035* (2013.01)
USPC ...................................... 600/201

(58) Field of Classification Search
USPC .......... 600/201–242; 606/72, 73, 61, 104, 96, 606/99, 246, 277, 279
See application file for complete search history.

(56) References Cited

U.S. PATENT DOCUMENTS

| | | |
|---|---|---|
| 3,129,706 A | 4/1964 | Reynolds |
| 3,486,505 A | 12/1969 | Morrison |
| 5,242,443 A | 9/1993 | Kambin |
| 5,431,658 A | 7/1995 | Moskovich |
| 5,496,321 A | 3/1996 | Puno |
| 5,545,165 A | 8/1996 | Biedermann |
| 5,582,577 A | 12/1996 | Lund |
| 5,685,826 A | 11/1997 | Bonutti |
| 5,797,911 A | 8/1998 | Sherman |
| 5,902,231 A | 5/1999 | Foley et al. |
| 5,944,658 A | 8/1999 | Koros et al. |
| 6,063,088 A | 5/2000 | Winslow |
| 6,083,225 A | 7/2000 | Winslow et al. |
| 6,099,547 A | 8/2000 | Gellman et al. |
| 6,102,951 A | 8/2000 | Sutter |
| 6,146,385 A | 11/2000 | Torrie et al. |
| 6,187,000 B1 | 2/2001 | Davison et al. |
| 6,200,322 B1 | 3/2001 | Branch et al. |
| 6,206,826 B1 | 3/2001 | Mathews et al. |
| 6,270,501 B1 | 8/2001 | Freiberg et al. |
| 6,280,442 B1 | 8/2001 | Barker |
| 6,358,253 B1 | 3/2002 | Torrie et al. |
| 6,360,750 B1 | 3/2002 | Gerber et al. |
| 6,478,800 B1 | 11/2002 | Fraser et al. |
| 6,485,494 B1 | 11/2002 | Haider |
| 6,530,926 B1 | 3/2003 | Davison |
| 6,530,929 B1 | 3/2003 | Justis et al. |

(Continued)

FOREIGN PATENT DOCUMENTS

WO  WO 2007/084641  7/2007

OTHER PUBLICATIONS

U.S. Appl. No. 12/941,143, filed Nov. 8, 2010.

*Primary Examiner* — Sunil K Singh
(74) *Attorney, Agent, or Firm* — Carter, DeLuca, Farrell & Schmidt, LLP

(57) ABSTRACT

A retraction device comprises a base and at least one retracting blade. The base has at least one tab. The retracting blade has a slotted distal end for receiving the tab of the base.

17 Claims, 3 Drawing Sheets

(56) References Cited

U.S. PATENT DOCUMENTS

| | | |
|---|---|---|
| 6,616,605 B2 | 9/2003 | Wright |
| 6,652,533 B2 | 11/2003 | O'Neil |
| 6,669,729 B2 | 12/2003 | Chin |
| 6,740,091 B2 | 5/2004 | Kohrs et al. |
| 6,743,206 B1 | 6/2004 | Smith |
| 6,755,841 B2 | 6/2004 | Fraser et al. |
| 6,796,422 B1 | 9/2004 | Lu |
| 6,800,084 B2 | 10/2004 | Davison et al. |
| 6,849,064 B2 | 2/2005 | Hamada |
| 6,929,606 B2 | 8/2005 | Ritland |
| 7,008,422 B2 | 3/2006 | Foley et al. |
| 7,011,660 B2 | 3/2006 | Sherman et al. |
| 7,056,321 B2 | 6/2006 | Pagliuca et al. |
| 7,083,621 B2 | 8/2006 | Shaolian et al. |
| 7,108,705 B2 | 9/2006 | Davison et al. |
| 7,144,393 B2 | 12/2006 | DiPoto et al. |
| 7,160,300 B2 | 1/2007 | Jackson |
| 7,166,107 B2 | 1/2007 | Anderson |
| 7,179,261 B2 * | 2/2007 | Sicvol et al. ............... 606/86 A |
| 7,188,626 B2 | 3/2007 | Foley et al. |
| 7,250,052 B2 | 7/2007 | Landry |
| 7,491,208 B2 * | 2/2009 | Pond et al. .................. 606/104 |
| 2003/0004401 A1 | 1/2003 | Ball |
| 2003/0191371 A1 | 10/2003 | Smith |
| 2004/0138662 A1 | 7/2004 | Landry et al. |
| 2004/0143265 A1 | 7/2004 | Landry et al. |
| 2005/0065517 A1 | 3/2005 | Chin |
| 2005/0131408 A1 * | 6/2005 | Sicvol et al. ..................... 606/61 |
| 2005/0131421 A1 | 6/2005 | Anderson et al. |
| 2005/0154389 A1 | 7/2005 | Selover et al. |
| 2005/0165408 A1 | 7/2005 | Puno et al. |
| 2005/0215999 A1 | 9/2005 | Birkmeyer et al. |
| 2006/0074445 A1 | 4/2006 | Gerber et al. |
| 2006/0200135 A1 | 9/2006 | Sherman et al. |
| 2006/0229614 A1 | 10/2006 | Foley et al. |
| 2006/0264962 A1 | 11/2006 | Chin et al. |
| 2007/0049931 A1 | 3/2007 | Justis et al. |
| 2007/0055247 A1 | 3/2007 | Jahng |
| 2007/0106123 A1 | 5/2007 | Gorek |
| 2007/0129731 A1 | 6/2007 | Sicvol et al. |
| 2007/0167954 A1 | 7/2007 | Sicvol et al. |
| 2008/0114403 A1 * | 5/2008 | Kuester et al. ............... 606/308 |
| 2008/0119849 A1 | 5/2008 | Beardsley et al. |
| 2009/0131755 A1 * | 5/2009 | White et al. ................. 600/210 |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |

* cited by examiner

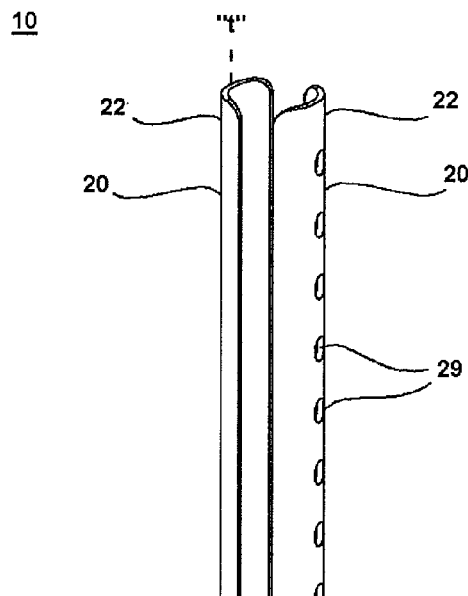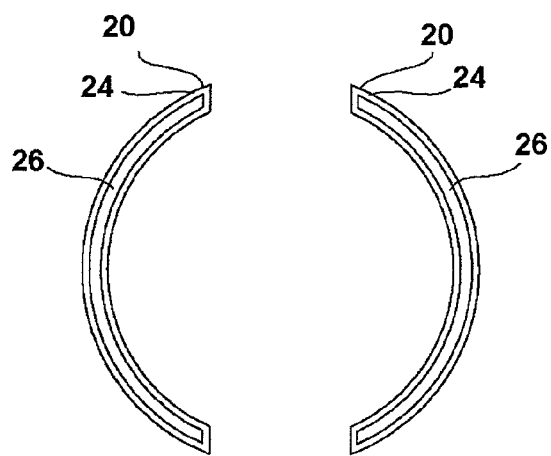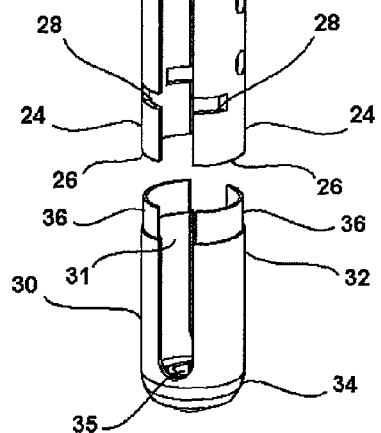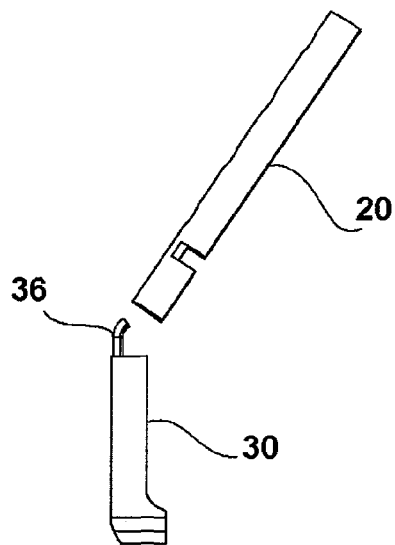
Fig. 1A
Fig. 1B
Fig. 1

MINIMALLY INVASIVE RETRACTION DEVICE HAVING DETACHABLE BLADES

CROSS-REFERENCE TO RELATED APPLICATIONS

This application claims priority to, and the benefit of, U.S. Provisional Patent Application No. 61/032,230, filed Feb. 28, 2008, the entire contents of which are incorporated herein by reference.

BACKGROUND

1. Technical Field

The present disclosure relates generally to orthopedic spine surgery and in particular to devices, systems and methods for a pedicle screw-based retractor to be used in a minimally invasive surgical approach.

2. Background of the Technology

There has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known in the prior art and can be modified to fit the contours of these small incisions, but they require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In recent years, minimally invasive surgical approaches have been applied to orthopedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e. liquid or gas) for distending tissue and creating working space for the surgeon. Surgery on the spine does not involve a capsule or space that can be so distended, instead involving multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition (i.e. as wide as practicable) for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly reduced post-operative pain, a shorter hospital stay, and a faster overall recovery.

Most spine implant procedures are open procedures, and while many manufacturers advertise a minimally invasive method, the procedure is typically not recommended for fusions and focuses on more common and accepted minimally invasive spine procedures such as kyphoplasty, vertebroplasty, and discectomy.

Medtronic Sofamor Danek's SEXTANT® is a minimally invasive device used for screw and rod insertion. Its shortcomings lie with how complicated the system is to use and the requirement for an additional incision for rod introduction. This system also requires that the guidance devices be rigidly fixed to the pedicle screw head in order to maintain instrument alignment and to prevent cross-threading of the setscrew. For these reasons, the surgeon cannot access the surrounding anatomy for complete preparation of the field. Nor does SEXTANT® allow for any variation in the procedure, if need be.

Depuy Spine's VIPER™ system is another minimally invasive implant and technique recommended for one or two level spine fusions. This system is less complicated than the SEXTANT® only requiring two incisions for a unilateral, one-level fusion, but it is limited in the same way as the SEXTANT® because it also requires the instrumentation to be rigidly fixed to the pedicle screw.

Spinal Concept's PATHFINDER® and NuVasive's SPHERX® spinal system (as disclosed in U.S. Pat. No. 6,802,844), are marketed as "minimally disruptive" spine fusion implants and procedures. While they have advantages over a general "open" procedure, they do not provide all of the advantages of a truly minimally invasive approach. Their characterization as "minimally open" procedures is a result of the inherent difficulty of introducing a rod in a minimally invasive spinal procedure. In order to introduce a rod long enough to accomplish a single level fusion, these systems describe an incision long enough to accept such a rod, thereby undermining the advantages of a minimally invasive approach.

The problem of rod introduction warrants further discussion as it is the central problem in minimally invasive spinal fusions. The systems currently on the market address this issue by adding another incision, using a larger incision, or avoiding fusions greater than one level.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

The present disclosure is directed to a retractor device, particularly a device used in spinal fusion surgery. The retractor device has a base and at least one retracting blade. The base has a tab and the retracting blade has a slot for receiving the tab of the base. It is also contemplated that the retracting blade has a slot for receiving a tab located on the base.

In embodiments, the retractor device includes two retracting blades and a base. Each retracting blade has an arcuate shape and is configured for positioning about the head of the pedicle screw and adapted to act as a cannula and guide the insertion of other instruments therethrough. The distal end of the retracting blades includes a slot. The base is configured for positioning about the head of a pedicle screw. The proximal end of the base includes a tab which may be made of a flexible or rigid material, or may be formed from a biocompatible frangible material so that it can break free from the base.

The tab of the base and the slot of the retracting blade have complimentary geometry so that they may be frictionally engaged and/or press fit together. The close fit allows for the manipulation of assembled retractor device without fear of unintentional separation. The retracting blades may be detached from the base by pulling up along the plane of alignment and disengaging the slot and tab. Alternatively, if the tabs are frangible, they may be broken off with the removal of the retracting blades leaving behind the base implanted with the pedicle screw.

BRIEF DESCRIPTION OF THE DRAWINGS

Embodiments of the presently disclosed retractor device are disclosed herein with reference to the drawings wherein:

FIG. 1 is a perspective view of the retractor device in accordance with the present disclosure;

FIG. 1A is a bottom view of the retracting blades of the retraction device of FIG. 1;

FIG. 1B is a partial side view of the retractor device of FIG. 1;

DETAILED DESCRIPTION OF THE EMBODIMENTS

Figure 1C:
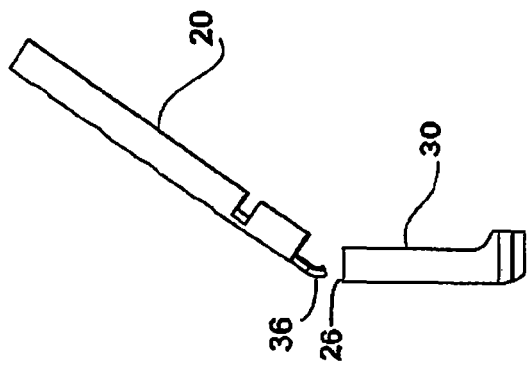
FIG. 1C is a partial side view of a retractor device in accordance with another embodiment of the present disclosure.

The retractor device of the present disclosure is used to conduct minimally invasive spine surgery. A pair of retracting blades are removeably attached to a base which encases a pedicle bone screw. The pedicle screw is used to guide the retractor device into place and act as a point of fixation with respect to the patient. A retracting device and systems and methods for use are disclosed in U.S. patent application Ser. No. 11/528,223 filed Sep. 26, 2006 (U.S. Patent Application Publication No. 2007/0106123), the entire contents of which are hereby incorporated by reference herein.

In the drawings and in the description that follows, the term "proximal," will refer to the end of a device or system that is closest to the operator, while the term "distal" will refer to the end of the device or system that is farthest from the operator.

Referring now to the drawings, in which like reference numerals identify identical or substantially similar parts throughout the several views, FIG. 1 illustrate a perspective view of the retractor device in accordance with the principles of the present disclosure. Retractor device 10 includes retracting blades 20 and retracting base 30. Retracting blades 20 are discussed singularly as they are substantially identical.

Retracting blade 20 includes proximal end 22 and distal end 24, and defines a longitudinal axis "t" extending along the length of the blade. Preferably, the cross-section of retracting blade 20 is a segment of a generally circular ring sector which provides stiffness to the retracting blade so that it will not yield to the counter force of the retracted tissue. Further, the arcuate or concave shape of retracting blade 20 is adapted and configured for positioning on base 30 as well as for guiding insertion of other instruments.

As shown in FIG. 1A, distal end 24 includes at least one slot 26 for receiving a tab 36 on base 30 for securing the retracting blade 20 to base 30. Slot 26 is a groove, channel, or other notch in retracting blade 20. Slot 26 may be circular, oval, oblong, square, rectangular, or any other shape as known in the art. Further, one or more slots 26 may be on distal end 24 of retracting blade 20. Alternatively, it is contemplated that the base 30 may include a slot 26 (shown in phantom) configured for receiving a tab 36 located on the retracting blade 20, as illustrated in FIG. 1C.

Retracting blade 20 may optionally include one or more living hinges 28 along proximal or distal ends 22, 24 so that retracting blade 20 may flex. The geometry encourages or allows retracting blade 20 to bend at living hinge(s) 28 and still be able to retract tissue that it is pressed against. More than one living hinge 28 may be incorporated to aid in bending along any portion of the blade's length.

Retracting blade 20 may also have one or more through holes 29 along axis "t". When two or more retracting blades 20 are used, standard surgical instruments, such as a Gelpi retractor, may be used to separate retracting blades 20 in order to retract skin and soft tissue and maintain the field of view. Alternatively, use of two or more retracting blades 20 also forms an internal channel whereby other surgical instruments may be placed between retracting blades 20 with excellent visibility of the screw head and the operative site, thereby facilitating the insertion of instruments and implants.

Retracting blade 20 may be a single monolithically formed unit or composed of several components connected to each other through conventional means, such as, for example, molding, casting, cutting, grinding, swaging, welding, or other techniques known to those skilled in the art. Retracting blade 20 may be form ed of any suitable medical grade material, including metals such as stainless steel, titanium, nickel-titanium, aluminum or alloys thereof, other rigid or semi-flexible materials, including polymeric materials such as polyetheretherketones, polycarbonate, polypropylene, and polyethylene; and composites thereof.

Retracting blade 20 may have a reflective or non-reflective coating, as appropriate to aid in increasing visibility in the wound or may have an artificial lighting feature. Retracting blade 20 may have a light emitting surface containing a light source such as a self-contained LED light engine or a channel for a fiber optic cable carrying light from a remote source. Further, the light emitting surface may be mounted on, integrally formed with, or faceted on retracting blade 20.

Base 30 is a u-shaped, cup-shaped, or bullet-shaped component adapted and configured for positioning about the head of a pedicle screw. Interior surface 31 preferably has a concave spherical geometry that mates with the head of a pedicle screw. Base 30 includes proximal end 32 and distal end 34. Distal end 34 has opening 35 for introduction of the pedicle screw therein. Proximal end 32 has tabs 36. Tab 36 may vary in number, length, angle, and size and accordingly, slot(s) 26 of retracting blade 20 will correspond to the size, number, and configuration of tab(s) 26 so that the retracting blade 20 and base 30 may be joined together.

Tab 36 may be made of a flexible material as shown in FIG. 1B. Further, tab 36 may be rigid or formed from a biocompatible frangible material so that it can break free from base 30 when retracting blade 20 is removed from the wound. Further, base 30 may be formed of any suitable medical grade material as described above for retracting element 20, particularly polymeric materials. Base 30 may be monolithically formed or composed of several components connected to each other through conventional means also described above.

Figure 2:
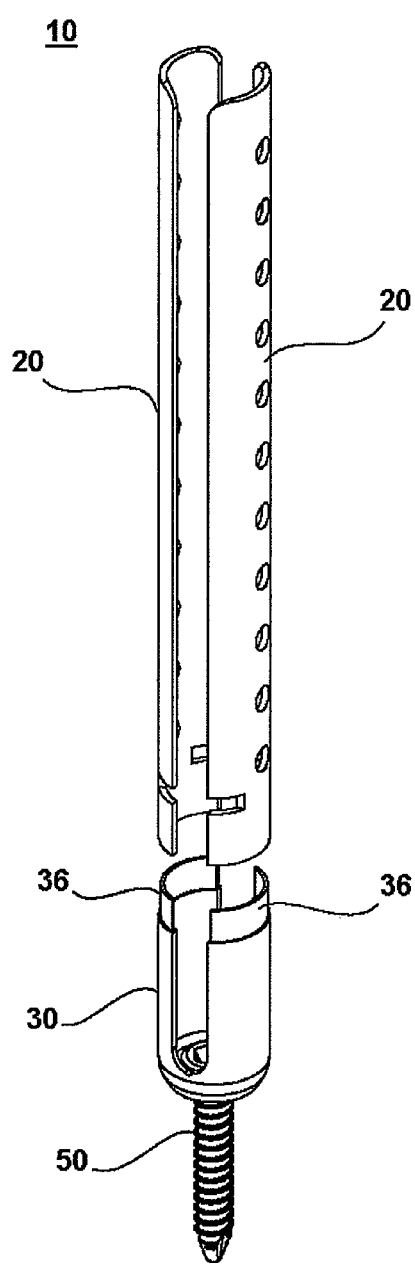
FIG. 2 is a perspective view of the retractor device with a pedicle screw in accordance with the present disclosure.
Figure 3:
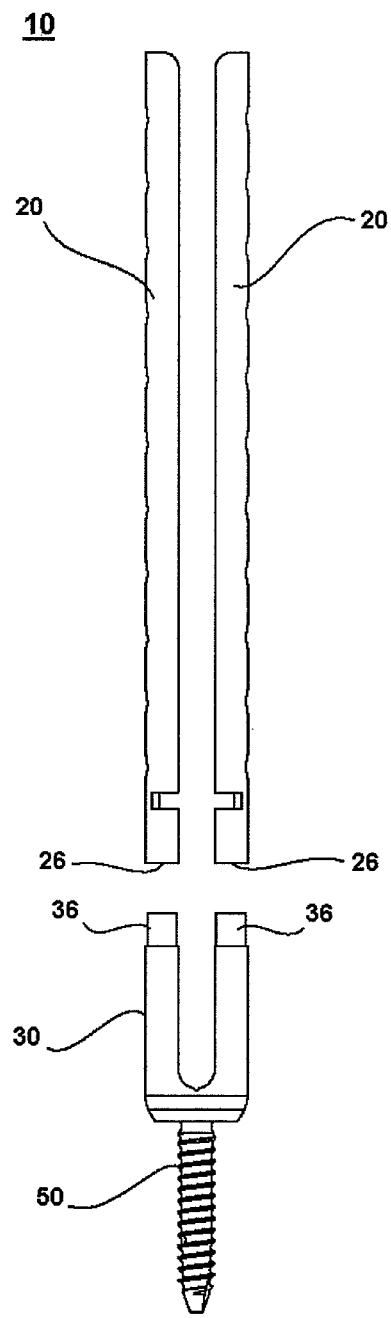
FIG. 3 is a side view of the retractor device of FIG. 2.

As illustrated in FIGS. 2 and 3, pedicle screw 50 and base 30 are placed together such that the bottom of base 30 is contiguous with the bottom of the head of pedicle screw 50 and the top of base 30 lies substantially flush with the top of the head of pedicle screw 50. This may be accomplished by sliding pedicle screw 50 within base 30 such that the head of the screw seats in the base with the threaded shank extending through opening 35. Alternatively, base 30 may be molded onto pedicle screw 50 or integrally formed therewith. Tabs 36 project therefrom. Retracting blade 20 and base 30 are joined by aligning slot 26 of retraction blade 20 with tab 36 of base 30 and coupling them together. The complimentary geometry of slot 26 and tab 36 create a press fit or friction fit. The friction fit allows for the manipulation of assembled retractor device 10 without fear of premature separation. If necessary or desired, blade 20 may be attached by gluing, ultrasonic welding, crimping, staking, or the like to assure sufficient engagement of the two to perform as a retractor during surgery, and yet be removable when such retraction is no longer desired or required. It is contemplated that the retracting blade 20 may be attached to base 30 prior to insertion of the screw or after the screw has been positioned in the operative site.

As will be appreciated, the pedicle screw may be cannulated such that it may be translated along a gude wire, thereby facilitating insertion of the pedicle screw and the retractor device into the work site. In addition, it is contemplated that conventional insertion tools or those disclosed in U.S. patent application Ser. No. 12/104,653, filed on Apr. 17, 2008 (U.S. Patent Application Publication No. 2008/0262318), the entire contents of which are hereby incorporated by reference, may be used in conjunction with the presently disclosed retractor devices and pedicle screws.

Preferably, retractor device 10 is implanted with retracting blade 20 and base 30 pre-assembled on pedicle screw 50. Alternatively, retracting blade 20 may be joined to base 30 after pedicle screw 50 is implanted with base 30.

In one embodiment, base 30 is made from a more flexible material than retracting blade 20, such that base 30 will flex at or below the connection point between retracting blade 20 and base 30. Flexing of retracting blade 20 below the juncture with base 30 provides enhanced access and visibility around the head of pedicle screw 50. When base 30 is made from a less flexible material than retracting blade 20, the flexing of retracting blade 20 will occur at a higher point.

Retracting blades 20 may be detached from base 30 by pulling up along the plane of alignment and disengaging slot 26 from tab 36. Alternatively, if tabs 36 are frangible, they may be broken off with retracting blades 20 leaving behind base 30 implanted with pedicle screw 50.

Retractor device 10 may be constructed as shown, or in reverse so that tabs are on the retracting blade and slots are in the base. Further, the number, length, angle, and size of the tabs may vary and accordingly, the slots will correspond to the size, number, and configuration of the tabs so that the retracting blade and the base may be joined together.

Multiple retracting blades may be used in conjunction with a single base to allow retraction in multiple directions and multiple retracting blades may be used with multiple bases, respectively, during a single spine procedure. The retractor device may be manufactured for a single use or can be sterilized and reused.

As with any surgical instrument and implant, the retractors must have the ability to be sterilized using known materials and techniques. Parts may be sterile packed by the manufacturer or sterilized on site by the user. Sterile packed parts may be individually packed or packed in any desirable quantity. For example, a sterile package may contain one or a plurality of retractors in a sterile enclosure. Alternatively, such a sterile surgical kit may also include one or a plurality of bone biopsy needle(s), Jamshidi needle(s), guide wires, sterile cannulated scalpels, dilators, rods, or other surgical instruments.

The blades may be made of a light transmitting material. The retractor may include a light guide system. The light guide system has an input adapter to receive light from a light source and one or more light emitting surfaces to illuminate the surgical field.

Figure 4:
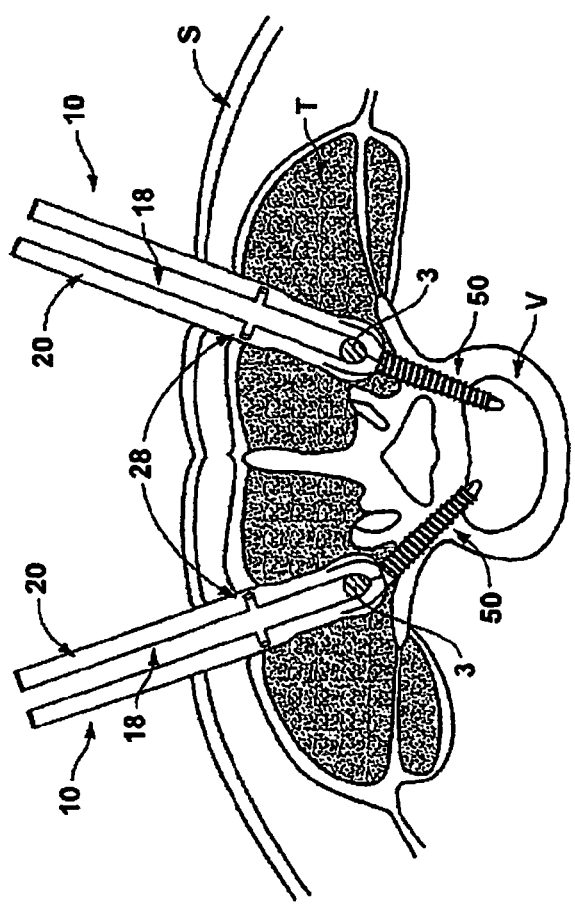
FIG. 4 is a front cross-sectional view of a vertebral body with a pair of minimally invasive retractors attached using screws with the blades in their initial position and rods positioned in the passages of the minimally invasive retractors.

A method for use of the presently disclosed system will now be described with reference to FIG. 4. Retractor device 10 is assembled with pedicle screw 50 as shown in FIG. 4. The assembled apparatus is inserted into an incision through the patient's skin S and muscle/fat tissue T such that pedicle screw 50 is subsequently threaded into a vertebral body V. Once the desired number of screws with retractor devices 10 are affixed to vertebral bodies V, retracting blades 20 are spread and/or pivoted apart to retract skin S and tissue T to create a retracted area at the target site. A rod 3 is inserted in a passage 18 when passage 18 is in an expanded state (i.e., tissue has been retracted). In a preferred method, the rod may be inserted along a path from one screw head to another, possibly subcutaneously such that it may be secured to fastening regions of pedicle screws in adjacent vertebral bodies. The retractor devices of the present disclosure are well suited for such a technique due to the unique access provided. Once the screw-rod construct is complete, retractor device 10 is removed from the patient as described above by separating the retracting blades 20 from the base 30. As such, the physician is able to create the desired working space using the retracting blades 20 and subsequently remove them from the operating site, while the base 30 remains in the working space with the pedicle screw 50. The separated portions may be moved away from the center line of the screw to provide clearance around the screw head, and then pulled out of the incision. This may be done by hand or with suitable gripping tools. An example of a retractor extracting tool is described in U.S. patent application Ser. No. 11/528,223 (referenced hereinabove). As such, retractor device 10 is separated from pedicle screw 50 without imparting significant downward or rotational forces against the patient's body. Retractor device 10 may then be removed from the patient and this process may be repeated for each installed retractor device 10.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

For example, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, or otherwise to access a surgical target site over a guidewire, the dilator, scalpel and retractors (or some of them) of the present disclosure may be used, with or without a bone screw.

What is claimed is:

1. A retraction device comprising:
   a base configured and dimensioned to receive and surround a head of a surgical screw such that a threaded shaft of the screw protrudes distally from the base, the base having at least one tab extending from a proximal portion of the base; and
   at least one retracting blade including a flexible body defining a longitudinal axis and including a distal end having a slot formed therein for receiving the tab of the base, a distal-most end of the retracting blade defining an opening of the slot and an entire length of the slot extending along the longitudinal axis, the slot being dimensioned to maintain a friction fit with the tab for releasably coupling the retracting blade with the base.

2. The retraction device of claim 1, wherein the surgical screw is a pedicle screw.

3. The retraction device of claim 1, wherein the at least one retracting blade includes a plurality of holes adapted for cooperation with a surgical instrument.

4. The retraction device of claim 1, wherein the surgical screw is cannulated.

5. The retraction device of claim 1, wherein the at least one retracting blade has an arcuate shape.

6. The retraction device of claim 1, wherein the at least one retracting blade includes at least one living hinge.

7. The retraction device of claim 1, wherein the at least one tab of the base is frangible.

8. The retraction device of claim 1, including two retracting blades.

9. The retraction device of claim 1, wherein the at least one tab extends from a proximal-most end of the base.

10. A retraction device comprising:
    a base configured and dimensioned to receive and surround a head of a surgical screw such that a threaded shaft of the screw protrudes distally from the base, the base having at least one slot formed in a proximal portion of the base with a proximal-most end of the base defining an opening of the at least one slot; and
    at least one retracting blade defining a longitudinal axis and including a distal end having a tab engageable with the at least one slot of the base, an entire length of the slot extending along the longitudinal axis of the retracting blade, the slot being dimensioned to maintain a friction fit with the tab for releasably attaching the retracting blade to the base, the at least one retracting blade bendable relative to the base.

11. The retraction device of claim 10, wherein the at least one retracting blade includes a plurality of holes adapted for cooperation with a surgical instrument.

12. The retraction device of claim 10, wherein the surgical screw is cannulated.

13. The retraction device of claim 10, wherein the at least one retracting blade has an arcuate shape.

14. The retraction device of claim 10, wherein the at least one retracting blade includes at least one living hinge.

15. The retraction device of claim 10, wherein the tab of the at least one retracting blade is frangible.

16. The retraction device of claim 10, including two retracting blades.

17. The retraction device of claim 10, wherein the tab extends from a distal-most end of the at least one retracting blade.

* * * * *